(12) United States Patent
Mitsuhashi et al.

(10) Patent No.: US 6,777,224 B2
(45) Date of Patent: Aug. 17, 2004

(54) METHOD FOR PRODUCING OPTICALLY ACTIVE MANDELIC ACID DERIVATIVES

(75) Inventors: Kazuya Mitsuhashi, Niigata (JP); Hiroaki Yamamoto, Ibaraki (JP)

(73) Assignee: Daicel Chemical Industries, Ltd., Osaka (JP)

( * ) Notice: Subject to any disclaimer, the term of this patent is extended or adjusted under 35 U.S.C. 154(b) by 51 days.

(21) Appl. No.: 10/278,268

(22) Filed: Oct. 23, 2002

(65) Prior Publication Data

US 2003/0119173 A1 Jun. 26, 2003

(51) Int. Cl.$^7$ .............................. C07C 1/00; C12P 41/00
(52) U.S. Cl. ....................... 435/280; 435/128; 435/130; 435/829; 435/830; 435/840; 435/843; 435/853; 435/859; 435/930; 435/940
(58) Field of Search ................................. 435/280, 930, 435/940, 829, 830, 840, 843, 853, 859, 128, 130

(56) References Cited

FOREIGN PATENT DOCUMENTS

| EP | 0 449 648 A2 A3 | 10/1991 | ............ C12P/41/00 |
|---|---|---|---|
| EP | 0 486 289 A2 A3 | 5/1992 | ............. C12P/7/42 |
| EP | 0 596 466 A2 A3 | 5/1994 | ............ C12P/41/00 |
| JP | 57-198096 A | 12/1982 | |
| JP | 6-7179 A | 1/1994 | |

OTHER PUBLICATIONS

Miyamoto, K. et al., "Enantioselective Oxidation of Mandelic Acid Using a Phenylmalonate Metabolizing Pathway of a Soil Bacterium *Alcaligenes bronshisepticus* KU 1201" *Biotechnology Letters* 14(5):363–366 (1992).

Gu Jian Xin, et al. "Reductive Biotransformation of Carbonyl Compounds—Application of Fungus, *Geotrichum sp.* G38 in Organic Synthesis" *Tetrahedron* 49(26):5805–5816 (1993).

*Primary Examiner*—David A. Redding
(74) *Attorney, Agent, or Firm*—Lahive & Cockfield LLP; Elizabeth A. Hanley, Esq.

(57) ABSTRACT

The present invention provides a method for enzymatically producing optically active mandelic acid derivatives. An optically active mandelic acid derivative (shown as Formula II) is produced by reacting a culture or cell body of a microorganism, or processed products thereof, with a phenylglyoxylic acid derivative, and then recovering the obtained optically active mandelic acid derivative, wherein the microorganism has the ability to stereo-selectively reduce the phenylglyoxylic acid derivative. An optically active mandelic acid obtained according to the present invention is useful as an intermediate for the synthesis of pharmaceuticals and agricultural chemicals.

Formula (II)

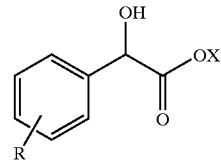

9 Claims, No Drawings

METHOD FOR PRODUCING OPTICALLY ACTIVE MANDELIC ACID DERIVATIVES

FIELD OF THE INVENTION

The present invention relates to a method for producing optically active mandelic acid derivatives that are widely used as raw materials or synthetic intermediates of various pharmaceuticals.

BACKGROUND OF THE INVENTION

As methods for producing optically active mandelic acids that have substituent(s) on the benzene ring, following methods are known:

- an optical resolution method by fractional crystallization of racemates (Unexamined Published Japanese Patent Application No. (JP-A) 2001-72644);
- an optical resolution method by chromatography (Journal of Chromatography. (1983), 282, 83–8);
- a method using nitrilase (JP-A Hei 4-99496 and JP-A Hei 6-237789);
- a method for obtaining an optically active substance by oxidizing one of the racemates (JP-A Hei 6-165695); and
- a method using hydroxylnitrile lyase (JP-A 2001-354616).

The optical isomers of interest are recovered through optical resolutions by fractional crystallization of racemates and by chromatography. On the other hand, the undesired enantiomers cannot be utilized, which leads to a loss of a part of raw material. That is, a raw material cannot be used efficiently according to these methods, which causes an increase in the cost of production. Similarly, when an optically active substance is obtained through the oxidation of one of the racemates, the optically active substance of interest is recovered while the undesired enantiomers cannot be utilized, which again causes an increase in the cost. Although a method wherein the undesired enantiomers are recovered and racemized to be recycled as the raw material has been reported, it requires complicated operation.

The production method that uses nitrilase requires a mandelonitrile derivative as the raw material. Hydrocyanic acid is necessary for the synthesis of a mandelonitrile derivative. In the method using hydroxynitrile lyase, benzaldehyde and sodium cyanide are used as raw materials. Due to its toxicity, hydrocyanic acid must be handled with care.

Enzymes not only have high catalytic functions, but also display stereospecificities, as well as substrate specificities and reaction specificities. Most stereo-specificities of enzymes are absolute, although with some exceptions.

As recent researches have become more exact, the importance of using optically active substances has been increased in the fields of pharmaceuticals, agricultural chemicals, feedstuffs, and aroma chemicals. This is because optical isomers sometimes have completely different biological activities. For example, while D(R)-thalidomide does not have teratogenicity, L(S)-form thalidomide has strong teratogenicity, and the practical use of the racemate of thalidomide caused drug induced suffering. Often time one of the enantiomers displays effective biological activity and the other not only lacks the activity but also competitively inhibits the effective enantiomer. This results in a drastic decrease in the biological activity of the racemate to less than ½ of the activity of the effective enantiomer. Therefore, obtaining (synthesizing or resolving) an optically pure enantiomer is an important industrial task. Aiming at this purpose, a technique wherein a racemate is synthesized and then effectively optically resolved has been widely used; and enzymatic optical resolutions that do not generate by-products or large quantity of waste fluid have been attracting attention.

Methods for obtaining optically active mandelic acids, wherein phenylglyoxylic acids that have no substituent on the benzene ring are asymmetrically reduced by microorganisms, are known in the art (See JP-A Sho 57-198096, JP-A Sho 57-198097, JP-A Sho 63-32492, JP-A Hei 6-7179, etc.).

A method that allowed for the production by enzymatic reaction of optically active mandelic acids that have substituent(s) on the benzene ring would be of great utility. However, until now, no enzymatic methods that can be performed on an industrial scale are known.

SUMMARY OF THE INVENTION

An object of the present invention is to provide an enzymatic method for producing optically active mandelic acids that have substituent(s) on the benzene ring.

The present inventors have vigorously investigated methods that satisfy such a high level requirement, and discovered that optically active mandelic acid derivatives that have substituent(s) on the benzene ring (hereinafter, referred to as mandelic acid derivatives) can be advantageously derived from phenylglyoxylic acid derivatives that have substituent (s) on the benzene ring (hereinafter, referred to as phenylglyoxylic acid derivatives) by the asymmetric reduction utilizing the reducing power of microorganisms.

As described above, methods for obtaining optically active mandelic acids by asymmetrical reduction of phenylglyoxylic acids that have no substituent on the benzene ring using microorganisms are known in the art. However, it is generally difficult to expect the same microorganisms to catalyze similar reactions with a different substrate, namely a phenylglyoxylic acid having a substituent on the benzene ring. The analogous reaction is not expected to occur due to the differences in steric hindrance by the substituent, toxicity of the substrate compound or the products to the microorganisms, as well as the difference in electronic effect of the substrate due to the substituent(s). For example, as is apparent from the Example described below, Candida famata IFO 0856 (JP-A Hei 6-7179) that act on phenylglyoxylic acid derivatives with no substituent cannot act on orthochlorophenylglyoxylic acid of the formula (I). This compound has the structure of a phenylglyoxylic acid derivative with a chlorine (Cl) substitution at ortho position of the benzene ring.

Therefore, the findings obtained by the present inventors were quite unexpected. More surprisingly, the optical purity of the optically active mandelic acids produced by the microorganisms was very high, at a level which implies no problem for practical use. Based on these findings, the inventors have accomplished the present invention.

Specifically, the present invention relates to a method for producing optically active mandelic acids as described below:

[1] a method for producing an optically active mandelic acid derivative, which comprises the steps of:

(a) reacting a culture or cell bodies of a microorganism, or processed products thereof that can steroselectively reduce a phenylglyoxylic acid derivative of the formula (I) with said phenylglyoxylic acid derivative of the formula (I):

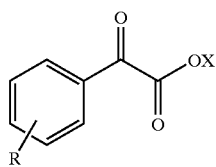

Formula I wherein: X is hydrogen, alkali metal, or alkaline earth metal; R indicates one or more substituents at ortho, meta, or para position, wherein the substituent is halogen, hydroxyl group, alkyl group having 1 to 3 carbon atoms, alkoxy group, thioalkyl group, amino group, nitro group, mercapto group, phenyl group, or phenoxy group, (b) stereo-specifically reducing said phenylglyoxylic acid derivative with the microorganism culture, cell bodies, or processed products to yield an optically active mandelic acid derivative of the formula (II):

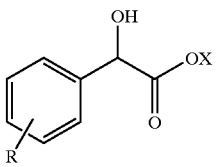

Formula II wherein: X and R is defined for formula (I), and (c) recovering said optically active mandelic acid derivative;

[2] the method for producing an optically active mandelic acid derivative according to [1], wherein the resulting optically active mandelic acid is in the (R)-form, and the microorganism belongs to any of the genus selected from the group consisting of:

Candida;
Cryptococcus;
Hansenula;
Ogataea;
Pichia;
Rhodosporidium;
Rhodotorula;
Saccharomyces;
Trichosporon;
Yamadazyma;
Rhodococcus;
Amycolatopsis;
Alcaligenes;
Arthrobacter;
Brevibacterium;
Comamonas;
Corynebacterium;
Enterobacter,
Enterococcus;
Lactobacillus;
Leuconostoc;
Microbacterium;
Micrococcus;
Proteus; and
Pseudomonas;

[3] the method for producing an optically active mandelic acid derivative according to [2], wherein the microorganism is selected from the group consisting of:

*Candida ernobii;*
*Candida gropengiesseri;*
*Candida magnoliae;*
*Candida sake;*
*Candida shehatae;*
*Candida silvatica;*
*Cryptococcusflavus;*
*Cryptococcus humicolus;*
*Cryptococcus marcerans;*
*Hansenula beckii;*
*Hansenula canadensis;*
*Hansenula glucozyma;*
*Ogataea pini;*
*Pichia carsonii;*
*Pichia fabianii;*
*Pichia haplophila;*
*Pichia subpelliculosa;*
*Rhodosporidium dacryodium;*
*Rhodosporidium diobovatum;*
*Rhodosporidium toruloides;*
*Rhodotorula glutinis;*
*Rhodotorula minuta;*
*Rhodotorula rubra;*
*Saccharomyces cerevisiae;*
*Trichosporon brassicae;*
*Trichosporon pullulans;*
*Yamadazyma castillae;*
*Yamadazyma nakazawae* var. *akitaensis;*
*Yamadazyma scolyti;*
*Rhodococcus erythropolis;*
*Rhodococcus fascians;*
*Rhodococcus obuensis;*
*Rhodococcus rhodochrous;*
*Amycolatopsis orientalis* subsp. *orientalis;*
*Alcaligenes* sp.;
*Arthrobacter protophormiae;*
*Brevibacterium iodinum;*
*Comamonas testosteroni;*
*Corynebacterium ammoniagenes;*
*Enterobacter cloacae;*
*Enterococcus casseliflavus;*
*Enterococcus faecalis;*
*Enterococcus hirae;*
*Lactobacillus viridescens;*
*Lactobacillus mali;*
*Lactobacillus collinoides;*
*Lactobacillus fructivorans;*
*Lactobacillus hilgardii;*
*Leuconostoc mesenteroides* subsp. *dextranicum;*
*Micrococcus luteus;*
*Proteus vulgaris*; and
*Pseudomonas diminuta;*

[4] the method for producing an optically active mandelic acid derivative according to [1], wherein the resulting optically active mandelic acid is in the (S)-form, and the microorganism belongs to any of the genus selected from the group consisting of:

Rhodosporidium;
Lactobacillus;
Leuconostoc;
Microbacterium; and
Pseudomonas;

[5] the method for producing an optically active mandelic acid derivative according to [4], wherein the microorganism is selected from the group consisting of:

*Rhodosporidium daryoidum;*
*Lactobacillus halotolerans;*
*Leuconostoc mesenteroides* subsp *cremoris;*
*Microbacterium lacticum;* and
*Pseudomonas* sp.;

[6] the method for producing an optically active mandelic acid derivative according to [1], wherein the phenylglyoxylic acid derivative of Formula I has at least one "R" substituent at the ortho position;

[7] the method for producing an optically active mandelic acid derivative according to [6], wherein the "R" substituent comprises a halogen at the ortho position;

[8] the method for producing an optically active mandelic acid derivative according to [1], wherein the phenylglyoxylic acid derivative of Formula I has at least one "R" substituent at the meta position; and

[9] the method for producing an optically active mandelic acid derivative according to [8], wherein the "R" substituent comprises a halogen at the meta position.

DETAILED DESCRIPTION OF THE INVENTION

The present invention is a method for producing an optically active mandelic acid derivative, comprising the steps of reacting a culture or cell bodies of a microorganism, or processed products thereof, with a phenylglyoxylic acid derivative of the above formula (I), wherein the microorganism has the ability to stereo-selectively reduce said compound; and recovering the optically active mandelic acid derivative of the formula (II).

In the present invention, the phrase "ability to stereoselectively reduce" refers to an ability to generate (R)- or (S)-mandelic acid derivative using a phenylglyoxylic acid derivative of the above formula (I) shown as the substrate. Any microorganism can be used in the present invention so long as it can generate the (R)-mandelic acid derivative or (S)-mandelic acid derivative. Microorganisms used in the present invention can be obtained by comparing the ability to generate (R)-mandelic acid derivative or (S)-mandelic acid derivative, for example, among microorganisms that belong to the genera shown below.

For example, a test microorganism is cultured in a medium containing the compound of formula (I), and the optical purity of the optically active mandelic acid derivative that is accumulated in the culture is measured. A microorganism for which the generation of the optically active mandelic acid is confirmed can be used in the present invention.

Alternatively, a test microorganism that has been grown in advance in a medium is collected, and is suspended in an appropriate buffer. Then, the microorganism is contacted and reacted with a phenylglyoxylic acid derivative represented by the formula (I), and the optical purity of the optically active mandelic acid derivative that is accumulated in the buffer is measured. If the generation of the optically active mandelic acid can be detected, said microorganism can be used in the present invention. According to this method, induction of an enzyme that metabolizes the compound of formula (I) can be expected by adding the compound in the medium for the culture of the test microorganism. Furthermore, addition of reduction energy during the reaction may increase the amount of accumulated product. Exemplary sources of reduction energy suitable for use in the present method include, but are not limited to, saccharides, alcohols, and sugar alcohols.

Needless to say, to obtain a product with high optical purity, it is advantageous to use a microorganism with a higher selectivity. Specifically, a microorganism that generates an optically active (R)-mandelic acid derivative or (S)-mandelic acid derivative with an optical purity of, for example, 80%, usually 95% or more, preferably 98% or more, and more preferably 99% or more, can be used.

"Optically active mandelic acid derivative" herein refers to a mandelic acid derivative that contains more of one optical isomer than it does of the other. According to the present invention, preferred optically active mandelic acid derivatives have an optical purity (enantiomeric excess; ee) of usually 50% ee or more, preferably 80% ee or more, more preferably 90% ee or more, and still more preferably 95% ee or more. The optical purity of an optically active mandelic acid derivative can be determined using, for example, an optical resolution column. "Optical isomers" of the present invention are generally referred to as "optically active substances" or "enantiomers".

For example, microorganisms that generate (R)-mandelic acid derivatives using as substrates phenylglyoxylic acid derivatives represented by the above formula (I) belong to a genus selected from the group consisting of:

Candida;
Cryplococcus;
Hansenula;
Ogataea;
Pichia;
Rhodosporidium;
Rhodotorula;
Saccharomyces;
Trichosporon;
Yamadazyma;
Rhodococcus;
Amycolatopsis;
Alcaligenes;
Arthrobacter;
Brevibacterium;
Comamonas;
Corynebactrium;
Enterobacter;
Enterococcus;
Lactobacillus;
Leuconostoc;
Microbacterium;
Micrococcus;
Proteus; and
Pseudomonas.

More specifically, examples of microorganisms belong to a genus selected from the group described above and which can generate (R)-mandelic acid derivatives with a high optical purity include the following:

*Candida ernobii;*
*Candida gropengiesseri;*
*Candida magnoliae;*
*Candida sake;*
*Candida shehatae;*
*Candida silvatica;*
*Cryptococcus flavus;*
*Cryptococcus humicolus;*
*Cryptococcus marcerans;*
*Hansenula beckii;*
*Hansenula canadensis;*
*Hansenula glucozyma;*
*Ogataea pini;*
*Pichia carsonii;*
*Pichia fabianii;*
*Pichia haplophila;*
*Pichia subpelliculosa;*
*Rhodosporidium dacryodium;*
*Rhodosporidium diobovatum;*
*Rhodosporidium toruloides;*
*Rhodotorula glutinis;*
*Rhodotorula minuta;*
*Rhodotorula rubra;*
*Saccharomyces cerevisiae;*
*Trichosporon brassicae;*
*Trichosporon pullulans;*
*Yamadazyma castillae;*
*Yamadazyma nakazawae* var. *akitaensis;*
*Yamadazyma scolyti;*
*Rhodococcus erythropolis;*
*Rhodococcus fascians;*
*Rhodococcus obuensis;*
*Rhodococcus rhodochrous;*
*Amycolatopsis orientalis* subsp. *orientalis;*
Alcaligenes sp.;
*Arthrobacter protophormiae;*
*Brevibacterium iodinum;*
*Comamonas testosteroni;*
*Corynebacterium ammoniagenes;*
*Enterobacter cloacae;*
*Enterococcus casseliflavus;*
*Enterococcus faecalis;*
*Enterococcus hirae;*
*Lactobacillus viridescens;*
*Lactobacillus mali;*
*Lactobacillus collinoides;*
*Lactobacillus fructivorans;*
*Lactobacillus hilgardii;*
*Leuconostoc mesenteroides* subsp. *dextranicum;*
*Micrococcus luteus;*
*Proteus vulgaris;* and
*Pseudomonas diminuta.*

Microorganisms that have the ability to convert phenylglyoxylic acid derivatives represented by the above formula (I) into optically active (S)-mandelic acid derivatives include those belonging to any of the genus selected from the group consisting of:

Rhodosporidium;
Lactobacillus;
Leuconostoc;
Microbacterium; and
Pseudomonas.

More specifically, examples of microorganisms that belong to a genus selected from the above group include:

*Rhodosporidium dacryoidum;*
*Lactobacillus halotorelans;*
*Leuconostoc mesenteroides* subsp. *cremoris;*
*Microbacterium lacticum;* and
*Pseudomonas sp.*

Microorganisms used in the present invention are available as cell strains from a variety of depositories. Depositories for cells include, for example, institutions such as:

IFO: Institute for Fermentation;
DSM: Deutsche Sammlung von Mikroorganismen;
ATCC: American Type Culture Collection;
JCM: Japan Collection of Microorganisms, The Institute of Physical and Chemical Research;
LAM: Institute of Applied Microbiology (LAM), The University of Tokyo; and
NRIC: NODAI Research Institute Culture Collection, Tokyo University of Agriculture. Alternatively, one skilled in the art can isolate required microorganisms from a variety of samples.

These microorganisms can be cultured based on information known in the field of zymology. Both synthetic and natural media can be used, so long as they contain an appropriate quantity of nutrients, such as carbon sources, nitrogen sources, and minerals. Both liquid culture media and solid media can be used. Optimum culture parameters may be readily determined by one skilled in the art using routine experimentation.

Specifically, one or more kinds of carbon sources are used by selecting, considering the assimilation property of the microorganism to be used, as needed from common carbon sources as shown below:

| saccharides: | glucose, fructose, maltose, galactose, etc. | natural carbohydrates: | starch, hydrolyzed starch, syrup, molasses, wheat, corn, etc. |
|---|---|---|---|
| alcohols: | glycerol, methanol, ethanol, etc. | fatty acids: | acetic acid, gluconic acid, pyruvic acid, citric acid, etc. |
| amino acids: | glycine, glutamine, asparagines, etc. | hydrocarbons | n-paraffin, etc. |

One or more kinds of nitrogen sources are used by selecting, considering the assimilation property of the microorganism to be used, as needed from common nitrogen sources as shown below:

organic nitrogen compounds:
meat extract, peptone, yeast extract, soybean hydrolysate, milk casein, casamino acid, various amino acids, corn steep liquor, other hydrolysate derived from animals, plants, microorganisms, etc.; and inorganic nitrogen compounds:
ammonia, ammonium nitrate, ammonium sulfate, ammonium salts such as ammonium chloride, nitrates such as sodium nitrate, urea, etc.

Inducers may be used to increase the ability of microorganisms to generate optically active mandelic acid derivatives. Depending on the microorganisms to be used, such inducers include optically active mandelic acid derivatives of interest, or phenylglyoxylic acid derivatives.

In addition, a small quantity of one or more kinds of inorganic salts, including for example, but not limited to, phosphate, hydrochloride, nitrate, acetate, and such of magnesium, manganese, potassium, calcium, sodium, cobalt, copper, zinc, and so on, can be used according to needs. Moreover, if necessary, anti-foaming agents, such as vegetable oils, surfactants, silicon, and the like, can be added into the culture solution.

The culture can be performed in a liquid medium containing components as described above, using conventional culture methods including, for example, shake culture, aeration culture, continuous culture, and fed batch culture.

Culture conditions may be selected as needed according to the type of the microorganism, the type of culture, and the culture method, and have no particular limitation so long as the said strain can grow and has the ability to convert phenylglyoxylic acid derivatives into mandelic acid derivatives under these conditions.

Usually, the pH at the initiation of the culture is preferably adjusted to a pH of 4 to 10, more preferably from 6 to 8, and the cultivation is conducted under a temperature of 15° C. to 70° C., preferably 25° C. to 40° C. The cultivation time is not limited, so long as cell bodies with the ability to convert phenylglyoxylic acid derivatives into mandelic acid derivatives can be obtained. Typical cultivation times ranges from about 1 day to 7 days, preferably from 1 day to 3 days.

Processed products of such cell bodies of the microorganisms include, for example, but are not limited to, lyophilized cell bodies, acetone-dried cell bodies, autolyzed cell bodies, cell body extracts, ground cell bodies, and sonicated cell bodies of said microorganism; additionally, enzymes purified from cell body extracts using a combination of known procedures can be also used. The enzymes contemplated by the present invention include both purified and partially purified enzymes.

For use in the present invention, cell bodies of the microorganism or processed products thereof of the present invention can be immobilized by known methods, such as those using polyacrylamide, sulfur containing polysaccharide gel (□-carrageenan gel), alginic acid gel, agarose gel, and ion exchange resin. However, the invention is not limited by such methods.

The asymmetric reduction method by a microorganism of the present invention can be performed by culturing the microorganism under appropriate culture conditions described above that allow the induction of enzyme(s), and then adding a reaction substrate to the obtained culture solution, or cell bodies collected from the culture solution or processed cell bodies. Alternatively, the asymmetric reduction can be performed concurrently with the culture under the same pH and temperature range as the culture conditions described above for 1 day to 7 days.

Suitable reaction conditions include, for example:
a pH of 4.0 to 9.0, preferably from 6.0 to 8.0;
a temperature of 15 to 50° C., preferably from 25 to 40° C.; and
a reaction time of 4 hours to 7 days.

In general, a better result can be expected by separating the culture of the microorganism from the asymmetric reduction.

In the latter reaction, a more efficient reaction can be expected by conducting the asymmetric reduction in the presence of saccharides, alcohols, or sugar alcohols, which serve as a source of reduction energy. Saccharides, including, but not limited to, glucose, fructose, and sucrose, can be used. Alcohols, including, but not limited to, ethanol, isopropanol, and glycerol, can be used. Solbitol may be mentioned as an optional sugar alcohol. The compound(s) serving as the source of the reduction energy can be added at an amount corresponding to the quantity of the reaction substrate, i.e., the phenylglyoxylic acid derivative.

When the pH of the reaction solution changes in accordance with the consumption of the reduction energy source, the pH may be adjusted within a certain range using suitable acids and alkalis which help to maintain a good reactivity.

When live cell bodies of microorganisms are used in the present invention, the addition of a surfactant into the reaction solution is preferable, since it shortens the reaction time. Surfactants used for this purpose are not particularly limited, so long as they increase the permeability of the cell walls of the live cell bodies. Examples include, but are not limited to, cetylpyrimidium bromide, cetyltrimethylammonium bromide, Triton X-100, paraisooctylphenyl ether, Tween 80, Span 60, etc. Preferably, a volume of 0.0001% to 1% of the reaction solution is used.

Similar effects can be achieved by adding an organic solvent into the reaction solution. The organic solvent used for this purpose is not particularly limited, so long as it increases the cell wall permeability of the live cell bodies, and includes toluene and xylene. Preferably, it is used at an amount of 0.0001% to 1% of the reaction solution.

Instead of adding a surfactant or an organic solvent into the reaction solution, cell bodies with increased cell wall permeability, which may be produced by pre-treatment with water or buffer that contain a surfactant and an organic solvent after collecting the cell bodies, can be used.

A phenylglyoxylic acid derivative of following formula (I) is used as a substrate in the method of the present invention:

Formula I

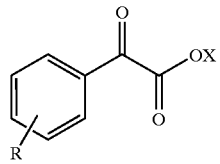

wherein: X is hydrogen atom, alkali metal or alkaline earth metal; R indicates one or more substituents at ortho, meta, or para position, wherein the substituent is halogen atom, hydroxyl group, alkyl group having 1–3 carbon atoms, alkoxy group, thioalkyl group, amino group, nitro group, mercapto group, phenyl group, or phenoxy group.

Exemplary "R" substituents include, but are not limited to, halogen atoms, such as bromine atom, chlorine atom, fluorine atom, and iodine atom; lower alkyl groups of 1 to 3 carbon atoms that may be branched; alkoxy groups, such as methoxy group and ethoxy group; thioalkyl groups, such as thiomethyl group; amino groups; nitro groups; mercapto groups; phenyl groups; and phenoxy groups. Two or more of these substituents may be introduced, and a ring may be formed, like lower alkylenedioxy groups, such as methylenedioxy group, ethylenedioxy group, and trimethylenedioxy group.

When the compound of the formula (I) is a metal salt, a metal atom, represented by X, is exemplified by a monovalent metal, such as sodium and potassium, and divalent metal, such as calcium and magnesium.

According to the present invention, orthohalophenylglyoxylic acid compounds, such as orthochlorophenylglyoxylic acid (wherein R at ortho position is Cl) and orthobromophenylglyoxylic acid, are examples of compounds of the formula (I) suitable for use in the method of the present invention.

Further, metahalophenylglyoxylic acid compounds, such as metachlorophenylglyoxylic acid (wherein R at meta position is Cl) and metabromophenylglyoxylic acid, can also be used.

Furthermore, compounds that have, apart from halogen, hydroxyl group (wherein R is OH), alkyl group (wherein R is methyl, ethyl, etc.), or such as the substituent can also be used.

These substrate compounds can be produced by known methods. For example, orthochlorophenylglyoxylic acid, shown in the Examples below, can be synthesized via orthochlorophenyloxoacetonitrile from orthochlorobenzoyl chloride as a starting material (Bull. Soc. Chim. Fr. 850, 851 (1959)).

A phenylglyoxylic acid derivative, the reaction substrate of the present invention, is preferably used at an appropriate concentration that allows for the efficient generation of the desired product. The phenylglyoxylic acid derivative is highly soluble in an aqueous solvent, and thus, can be used at a high concentration which does not inhibit the reaction. The concentration of the phenylglyoxylic acid derivative in the reaction solution may be, for example, 0.1% to 50% w/v, preferably 1% to 20% w/v. The phenylglyoxylic acid derivative may be added by any suitable method, including, but not limited to, adding in the block (batch method), adding in portions (fed batch method), or adding continuously (feed method).

In the asymmetric reduction of the present invention, by-products tend to increase under aerobic conditions. In such cases, a higher yield can be achieved by performing the reaction under anaerobic conditions or under oxygen-limited conditions. Specifically, an increased yield can be expected, for example, by bubbling nitrogen gas into the liquid or gas phase during the reaction.

The reaction conditions exemplified herein are suitable for the synthesis of both the (R)-form and the (S)-form mandelic acid derivatives. According to the present invention, the form of the optical isomer obtained depends on the type of the microorganism used for the method. Therefore, the conditions for the asymmetric reduction and the conditions for the culture of the microorganism used in the reaction should be properly adjusted according to the type of the microorganism. Optimum reaction and culture conditions may be readily ascertained by one skilled in the art using routine experimentation.

As described above, under the reaction of the present invention, a phenylglyoxylic acid derivative is asymmetrically reduced to generate an optically active mandelic acid derivative. The generated optically active mandelic acid derivative can be easily isolated by conventional methods. For example, following the removal of insoluble materials, such as cell bodies, from the reaction solution by centrifugation, the pH of the reaction solution is reduced, preferably adjusted to around a pH of 1, with an appropriate mineral acid, such as sulfuric acid or hydrochloric acid; the solution is extracted with ethyl acetate, methyl isobutyl ketone, diethyl ether, and so on; finally, the optically active mandelic acid derivative is obtained as crystal by concentrating the solution under reduced pressure.

In order to increase the purity of a reaction product, the product can be highly purified by dissolving it in a small quantity of acetone, and then subjecting to silica gel column chromatography eluted with a mixed hexane-acetone solvent. Alternatively, the reaction product can be easily separated from other impurities by dissolving it with heating in a mixed solvent of benzene, toluene or hexane, and ethyl acetate, followed by cooling and recrystallization.

Mandelic acid derivatives obtained by the present invention can be stored as follows. The present compounds can be stored and handled in crystals, i.e., in powders just as they are obtained. Usually, large amount of substances can be stored as powders with the smallest volume. To store mandelic acid derivatives as powders, conditions which cause least changes in the quality, particularly changes in the optical purity, over time are preferably selected. For example, it is preferable to store the materials at room or lower temperature, avoiding moisture. More preferably, at 0° C. or lower avoiding moisture.

However, when in the powder form, mandelic acid derivatives run the risk of dust explosion by static electricity. In order to avoid the risk of dust explosion, mandelic acid derivatives may be stored in solution form, dissolved in an appropriate solvent. Storage as a solution takes up more space as compared with equal amounts of substances stored in a dry state. However, an advantage can be expected that accommodations required for preparing powders, such as hopper needed for handling powders, is unnecessary. Thus, one skilled in the art can appropriately select storage conditions, according to the intended use of the mandelic acid derivatives.

For storage of mandelic acid derivatives, any solvent that can dissolve mandelic acid may be used. Such solvents include, but are not limited to, for example, in addition to water, buffers with adjusted pH, and a variety of organic solvents. More specifically, these solvents for storage include ethyl acetate, methyl isobutyl ketone, and such, as well as water. Since mandelic acid derivatives are acids, esters or alcoholic solvents may cause problems, such as reduction of the purity of the present compounds or generation of impurities by ester interchange or esterification. However, esters or alcoholic solvents can be used, when it is possible to prevent contamination of acids or alkalis that cause generation of impurities or reduction of the optical purity, or when deterioration in quality can be prevented by controlling the temperature and light.

Mandelic acid derivatives in the state of solution can be stored under conditions wherein at least their quality before use can be maintained. The term "quality" specifically refers to optical purity or purity of the mandelic acid derivatives. For example, when they arc in the state of aqueous solution, the alkaline condition is preferably avoided. Specifically, it is desirable that they are stored under a condition of a pH below 11, preferably under acidic to neutral conditions. Furthermore, in order to avoid degradation by heat, storage at low temperature is preferable. Specifically, suitable temperature for storage is usually 65° C. or lower, preferably 50° C. or lower, and more preferably 40° C. or lower.

According to the present invention, optically active mandelic acid derivatives can be efficiently produced by asymmetric reduction using microorganisms. A high yield can be expected according to the method of the present invention, and thus it is also advantageous in the industrial field. Optically active mandelic acid derivatives produced by the method of the present invention are useful as optical resolution agents, and as raw materials for syntheses of optically active pharmaceuticals and agricultural chemicals. More specifically, optically active mandelic acid derivatives are useful as intermediates in the syntheses of anti-platelet agents and antiobestic drugs, and in preferential crystallization.

EXAMPLES

The present invention is specifically illustrated below with reference to Examples, but it should not construed as being limited thereto.

Depositories for cell strains in the tables are shown below:
IFO: Institute for Fermentation;
DSM: Deutsche Sammlung von Mikroorganismen;
ATCC: American Type Culture Collection;
JCM: Japan Collection of Microorganisms, The Institute of Physical and Chemical Research;
LAM: Institute of Applied Microbiology (LAM), The University of Tokyo; and
NRIC: NODAI Research Institute Culture Collection, Tokyo University of Agriculture.

Example 1

Synthesis of Substrate Orthochlorophenylglyoxylic Acid

Orthochlorobenzoyl chloride (17.5 g, 0.1 mol), cuprous cyanide (11.65 g, 0.13 mol), and acetonitrile (8 mL) were refluxed in toluene (15 mL) for 3 hours, and were cooled to room temperature. Then, insoluble substances were removed through filtration, and the residue was washed with toluene. Solvent in the resulting filtrate was evaporated under reduced pressure, and the residue was distilled to obtain orthochlorophenyloxoacetonitrile (12.3 g, 75% yield).

The resulting orthochlorophenyloxoacetonitrile (16.5 g, 0.1 mol) was reacted in conc. hydrochloric acid (110 mL) at room temperature for 5 days, and then water (1100 mL) was added thereto. The reaction mixture was extracted with ether, solvent of the ether layer was evaporated under reduced pressure, and the residue was recrystallized in carbon tetrachloride to obtain white crystals (16.6 g).

This compound was identified to be orthochlorophenyl-lyoxylic acid of formula (III) by $^1$H-NMR, MS, and IR spectroscopic analyses (90% yield).

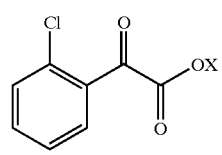

Formula III

Example 2

Screening for Yeasts 4-ml aliquots of liquid culture medium (pH 6.0) comprising yeast extract (3 g/L), malt extract (3 g/L), glucose (20 g/L), and polypeptone (5 g/L) were poured into test tubes (18 mm ϕ), respectively, and were heat sterilized in autoclave at 121° C. for 15 minutes. To each sterilized medium, one platinum loop of each of the cell strains shown in Table 1 below was inoculated, respectively, and was subjected to shake culture at 30° C. for 48 hours.

Cell bodies were collected by centrifugation from 2 mL of the obtained culture solution, 100 mM phosphate buffer (pH 7.0, 1 mL) containing orthochlorophenylglyoxylic acid (10 mg) and glucose (10 mg) was added thereto, and the mixture was reacted with shaking at 30° C. for 48 hours.

Cell bodies were removed from the reaction solution by centrifugation, and orthochloromandelic acid contained in the resulting supernatant was quantitatively assayed by liquid chromatography using a C18 reversed phase column. For quantification, the C18 reversed phase column (Wakosil II 5C18 HG, 4.6 mm×250 mm)(Wako Pure Chemical Industries, Ltd.) was used at a column temperature of 40° C., eluted with an eluent consisting of 50 mM phosphate buffer (pH 2.5): acetonitrile (3:1) at a flow rate of 1 mL/min, and the UV absorption of the eluate was measured at 254 nm.

Orthochloromandelic acid was extracted with ethyl acetate from the reaction solution, and after the solvent was removed, e optical purity of the orthochloromandelic acid was measured by liquid chromatography using an optical resolution column. As the optical resolution column, CHIRALCEL OJ-H (4.6 mm×150 mm)(Daicel Chemical Industries, Ltd.) was used with elution using an eluent consisting of n-hexane:isopropanol:trifluoroacetic acid (85:15:0.1) at a flow rate of 1.5 mL/min, and the UV absorption of the eluate was measured at 254 nm.

The results of the analyses are shown in Table 1. As a result, the generation of optically active (R)-orthochloromandelic acid was confirmed.

TABLE 1

| Cell strains | Accumulated product (g/L) | Optical purity (%) |
|---|---|---|
| Candida sake IFO 1517 | 0.661 | 100 |
| Candida shehatae IFO 1983 | 0.690 | 100 |
| Candida silvatica IFO 10311 | 1.27 | 99.8 |
| Candida magnoliae DSM 70638 | 0.784 | 92.0 |
| Candida ernobii DSM 70858 | 0.508 | 84.1 |
| Cryptococcus marcerans IFO 1870 | 3.68 | 100 |
| Cryptococcus flavus IFO 0407 | 3.06 | 100 |
| Cryptococcus humicolus IFO 0760 | 1.20 | 99.4 |
| Hansenula glucozyma DSM 70271 | 0.232 | 99.3 |
| Hansenula Canadensis DSM 70281 | 0.271 | 99.1 |
| Hansenula beckii DSM 70266 | 0.268 | 87.3 |
| Ogataea pini IFO 1342 | 0.654 | 100 |
| Pichia fabianii IFO 1253 | 0.242 | 98.4 |
| Pichia carsonii DSM 70392 | 0.675 | 97.5 |
| Pichia subpelliculosa IFO 0808 | 0.342 | 94.9 |
| Pichia haplophila DSM 70365 | 0.299 | 94.7 |
| Rhodosporidium toruloides IFO 1535 | 1.41 | 100 |
| Rhodosporidium diobovatum IFO 1830 | 1.16 | 100 |
| Rhodosporidium toruloides IFO 0559 | 2.92 | 96.2 |
| Rhodotorula rubra IFO 0383 | 0.635 | 100 |
| Rhodotorula glutinis IFO 0898 | 0.511 | 100 |
| Saccharomyces cerevisiae IFO 0203 | 0.166 | 94.0 |
| Trichosporon brassicae IFO 1584 | 1.49 | 100 |
| Trichosporon pullulans IFO 1232 | 0.339 | 100 |
| Yamadazyma castillae IFO 1823 | 1.21 | 100 |
| Yamadazyma scolyti IFO 1280 | 0.511 | 100 |
| Yamadazyma nakazawae var. akitaensis IFO 1669 | 0.454 | 96.0 |

Example 3

Screening for Bacteria and Actinomycetes 4-ml aliquots of broth medium (Nissui Pharmaceutical Co., Ltd.) were poured into test tubes (18 mm ϕ), respectively, and were heat sterilized in autoclave at 121° C. for 15 minutes. To each sterilized medium, one platinum loop of each of the cell strains shown in Table 2 below was inoculated, respectively, and was subjected to shake culture at 30° C. for 48 hours.

Cell bodies were collected by centrifugation from 2 mL of the obtained culture solution, 100 mM phosphate buffer (pH 7.0, 1 mL) containing orthochlorophenylglyoxylic acid (10 mg) and glucose (10 mg) was added thereto, and the mixture was reacted with shaking at 30° C. for 48 hours.

The cell bodies were removed from the reaction solution by centrifugation, orthochloromandelic acid contained in the resulting supernatant was quantitatively assayed, and the optical purity of the acid was measured according to the method of Example 2.

The results of the analyses are shown in Table 2. As a result, generation of optically active (R)-orthochloromandelic acid was confirmed.

TABLE 2

| Cell strains | Accumulated product (g/L) | Optical purity (%) |
|---|---|---|
| Amycolatopsis orientalis subsp. Orientalis IFO 12806 | 2.42 | 97.9 |
| Rhodococcus erythropolis JCM 6822 | 2.28 | 100 |
| Rhodococcus fascians IFO 12077 | 4.79 | 99.7 |
| Rhodococcus obuensis JCM 6048 | 2.72 | 99.4 |
| Rhodococcus rhodochrous DSM 363 | 1.42 | 100 |
| Alcaligenes sp. IAM 1015 | 1.47 | 97.8 |
| Arthrobacter protophormiae IFO 12128 | 5.31 | 98.7 |
| Brevibacterium iodinum IFO 3558 | 2.29 | 93.4 |
| Comamonas testosteroni IFO 12048 | 2.45 | 95.4 |
| Corynebacterium ammoniagenes IFO 12072 | 6.92 | 98.2 |
| Enterobacter cloacae IFO 3320 | 3.06 | 98.7 |
| Micrococcus luteus IFO 3333 | 2.00 | 100 |
| Proteus vulgaris IFO 3851 | 2.49 | 100 |
| Pseudomonas diminuta IFO 12697 | 2.76 | 98.7 |

Example 4

Screening for Lactic Acid Bacteria 4-ml aliquots of MRS medium (Lactobacilli MRS broth, Difco Laboratories) were poured into test tubes (18 mm φ), respectively, and were heat sterilized in autoclave at 121° C. for 15 minutes. To each sterilized medium, one platinum loop of each of the cell strains shown in Table 3 below was inoculated, respectively, and was subjected to shake culture at 30° C. for 48 hours.

Cell bodies were collected by centrifugation from 2 mL of the obtained culture solution, 100 mM phosphate buffer (pH 7.0, 1 mL) containing orthochlorophenylglyoxylic acid (10 mg) and glucose (10 mg) was added thereto, and the mixture was reacted with shaking at 30° C. for 48 hours.

The cell bodies were removed from the reaction solution by centrifugation, and orthochloromandelic acid contained in the resulting supernatant was quantitatively assayed, and the optical purity of the acid was measured according to the method of Example 2.

The results of the analyses are shown in Table 3. As a result, generation of optically active (R)-orthochloromandelic acid was confirmed.

TABLE 3

| Cell strains | Accumulated product (g/L) | Optical purity (%) |
|---|---|---|
| Enterococcus casseliflavus NRIC 0106 | 3.63 | 99.0 |
| Enterococcus faecalis IFO 12966 | 3.89 | 99.0 |
| Enterococcus hirae ATCC 49611 | 1.15 | 98.4 |
| Lactobacillus viridescens NRIC 1073 | 3.09 | 99.1 |
| Lactobacillus mali NRIC 1076 | 2.02 | 99.1 |
| Lactobacillus collinoides NRIC 1049 | 5.37 | 99.0 |
| Lactobacillus fructivorans NRIC 0224 | 5.22 | 98.9 |
| Lactobacillus hilgardii DSM 20051 | 8.06 | 98.8 |
| Leuconostoc mesenteroides subsp. dextranicum NRIC 1085 | 8.87 | 99.8 |

Example 5

Screening for Yeasts that Generate (S)-Form Mandelic Acid Derivatives 4-ml aliquots of liquid culture medium (pH 6.0) containing yeast extract (3 g/L); malt extract (3 g/L), glucose (20 g/L), and polypeptone (5 g/L) was poured into a test tube (18 mm φ), and was heat sterilized in an autoclave at 121° C. for 15 minutes. To the sterilized medium, one platinum loop of the cell strain shown in Table 4 below was inoculated, and was subjected to shake culture at 30° C. for 48 hours.

Cell bodies were collected by centrifugation from 2 mL of the obtained culture solution, 100 mM phosphate buffer (pH 7.0, 1 mL) containing orthochlorophenylglyoxylic acid (10 mg) and glucose (10 mg) was added thereto, and the mixture was reacted with shaking at 30° C. for 48 hours.

The cell bodies were removed from the reaction solution by centrifugation, orthochloromandelic acid contained in the resulting supernatant was quantitatively analyzed, and the optical purity of the acid was measured according to the method of Example 2.

The results of the analyses are shown in Table 4. As a result, generation of optically active (S)-orthochloromandelic acid was confirmed.

TABLE 4

| Cell strains | Accumulated product (g/L) | Optical purity (%) |
|---|---|---|
| Rhodosporidium daryoidum IFO 1930 | 0.417 | −74.0 |

Example 6

Screening for Bacteria and Actinomycetes that Generate (S)-Form Mandelic Acid Derivatives 4-ml aliquots of broth medium (Nissui Pharmaceutical Co., Ltd.) were poured into test tubes (18 mm φ), respectively, and were heat sterilized in autoclave at 121° C. for 15 minutes. To each sterilized medium, one platinum loop of each of the cell strains shown in Table 5 below was inoculated, respectively, and was subjected to shake culture at 30° C. for 48 hours.

Cell bodies were collected by centrifugation from 2 mL of the obtained culture solution, 100 mM phosphate buffer (pH 7.0, 1 mL) containing orthochlorophenylglyoxylic acid (10 mg) and glucose (10 mg) was added thereto, and the mixture was reacted with shaking at 30° C. for 48 hours.

The cell bodies were removed from the reaction solution by centriflugation, orthochloromandelic acid contained in the resulting supernatant was quantitatively assayed, and the optical purity of the acid was measured according to the method of Example 2.

The results of the analyses are shown in Table 5. As a result, generation of optically active (S)-orthochloromandelic acid was confirmed.

TABLE 5

| Cell strains | Accumulated product (g/L) | Optical purity (%) |
|---|---|---|
| *Microbacterium lacticum* IFO 14135 | 5.02 | −66.0 |
| *Pseudomonas* sp. ATCC 14676 | 1.34 | −39.1 |

Example 7

Screening for Lactic Acid Bacteria that Generate (S)-Form Mandelic Acid Derivatives 4-ml aliquots of MRS medium (Lactobacilli MRS broth, Difco Laboratories) were poured into test tubes (18 mm φ), respectively, and were heat sterilized in autoclave at 121° C. for 15 minutes. To each sterilized medium, one platinum loop of each of the cell strains shown in Table 6 below was inoculated, respectively, and was subjected to shake culture at 30° C. for 48 hours.

Cell bodies were collected by centrifugation from 2 mL of the obtained culture solution, 100 mM phosphate buffer (pH 7.0, 1 mL) containing orthochlorophenylglyoxyhc acid (10 mg) and glucose (10 mg) was added thereto, and the mixture was reacted with shaking at 30° C. for 48 hours.

The cell bodies were removed from the reaction solution by centrifugation, orthochloromandelic acid contained in the resulting supernatant was quantitatively assayed, and the optical purity of the acid was measured according to the method of Example 2.

The results of the analyses are shown in Table 6. As a result, generation of optically active (S)-orthochloromandelic acid was confirmed.

TABLE 6

| Cell strains | Accumulated product (g/L) | Optical purity (%) |
|---|---|---|
| *Lactobacillus halotolerans* NRIC 1627 | 1.32 | −100 |
| *Leuconostoc mesenteroides* subsp. *cremoris* IAM 1087 | 2.07 | −17.6 |

Comparative Example 4-ml liquid culture medium (pH 6.0) comprising yeast extract (3 g/L), malt extract (3 g/L), glucose (20 g/L), and polypeptone (5 g/L) was poured into a test tube (18 mm φ, and was heat sterilized in an autoclave at 121° C. for 15 minutes. To the sterilized medium, one platinum loop of *Candida famata* IFO 0856 described in Patent No.03146641 (JP-A Hei 6-7179) was inoculated, and was subjected to shake culture at 30° C. for 48 hours.

Cell bodies were collected by centrifugation from 2 mL of the obtained culture solution, 100 mM phosphate buffer (pH 7.0, 1 mL) containing orthochlorophenylglyoxylic acid (10 mg) and glucose (10 mg) was added thereto, and the mixture was reacted with shaking at 30° C. for 48 hours.

The cell bodies were removed from the reaction solution by centrifugation, and orthochloromandelic acid contained in the resulting supernatant was quantitatively assayed according to the method of Example 2.

As a result, no orthochloromandelic acid was detected.

Example 8

Synthesis of the Substrate, Metachlorophenylglyoxylic Acid

Metachlorobenzoyl chloride (43.8 g, 0.1 mol), cuprous cyanide (29.1 g, 0.13 mol), and acetonitrile (20 mL) in toluene (37 mL) were refluxed for 3 hours, and were cooled to room temperature. Then, insoluble substances were removed through filtration, and the residue was washed with toluene. Solvent in the resulting filtrate was evaporated under reduced pressure, and the residue was distilled to give metachlorophenyloxoacetonitrile (28 g, 68% yield).

The resulting metachlorophenyloxoacetonitrile (15 g, 0.1 mol) was reacted in conc. hydrochloric acid (110 mL) at room temperature for 5 days, and then water (1100 mL) was added thereto. The reaction mixture was extracted with ether, solvent in the ether layer was evaporated under reduced pressure, and the residue was recrystallized in carbon tetrachloride to obtain white crystals (15.1 g).

This compound was identified to be metachlorophenylglyoxylic acid represented by the formula (III) by $^1$H-NMR, MS, and IR spectroscopic analyses (90% yield).

Example 9

Screening for Bacteria 2

4-ml aliquots of broth medium (Nissui Pharmaceutical Co., Ltd.) were poured into test tubes (18 mm φ), respectively, and were heat sterilized in autoclave at 121° C. for 15 minutes. To each sterilized medium, one platinum loop of each of the cell strains shown in Table 7 below was inoculated, respectively, and was subjected to shake culture at 30° C. for 48 hours.

Cell bodies were collected by centrifugation from 2 mL of the obtained culture solution, 100 mM phosphate buffer (pH 7.0, 1 mL) containing metachlorophenylglyoxylic acid (10 mg) and glucose (10 mg) was added thereto, and the mixture was reacted with shaking at 30° C. for 48 hours.

The cell bodies were removed from the reaction solution by centrifugation, and metachloromandelic acid contained in the resulting supernatant was quantitatively assayed by liquid chromatography using a C18 reversed phase column. For quantification, the C18 reversed phase column (Wakosil II 5C18 HG, 4.6 mm×250 mm)(Wako Pure Chemical Industries, Ltd.) was used at a column temperature of 40° C. with elution using an eluent consisting of 50 mM phosphate buffer (pH 2.5):acetonitrile (3:1) at a flow rate of 1 mL/min, and the UV absorption of the eluate was measured at 254 mm.

Metachloromandelic acid was extracted with ethyl acetate from the reaction solution, and after the solvent was removed, the optical purity of the metachloromandelic acid was measured with liquid chromatography using an optical resolution column. As the optical resolution column, CHIRALCEL OJ-H (4.6 mm×150 mm)(Daicel Chemical Industries, Ltd.) was used with elution using an eluent consisting of n-hexane:isopropanol:trifluoroacetic acid (85:15:0.1) at a flow rate of 1.5 mL/min, and the UV absorption of the eluate was measured at 254 nm.

The results of the analyses are shown in Table 7. As a result, generation of optically active (R)-metachloromandelic acid was confirmed.

TABLE 7

| Cell strains | Accumulated product (g/L) | Optical purity (%) |
| --- | --- | --- |
| *Enterobacter cloacae* IFO 3320 | 1.09 | 99.0 |
| *Arthrobacter protophormiae* IFO 12128 | 3.06 | 98.8 |

Example 10

Screening for Lactic Acid Bacteria 2

4-ml aliquots of MRS medium (Lactobacilli MRS broth, Difco Laboratories) were poured into test tubes (18 mm φ), respectively, and were heat sterilized in autoclave at 121° C. for 15 minutes. To each sterilized medium, one platinum loop of each of the cell strains shown in Table 7 below was inoculated, respectively, and was subjected to shake culture at 30° C. for 48 hours, Cell bodies were collected by centrifugation from 2 mL of the obtained culture solution, 100 mM phosphate buffer (pH 7.0, 1 mL) containing metachlorophenylglyoxylic acid (100 mg) and glucose (100 mg) was added thereto, and the mixture was reacted with shaking at 30° C. for 48 hours.

The cell bodies were removed from the reaction solution by centrifugation, metachloromandelic acid contained in the resulting supernatant was quantitatively assayed, and the optical purity of the acid was measured according to the method of Example 8.

The results of the analyses are shown in Table 8. As a result, generation of optically active (R)-metachloromandelic acid was confirmed.

TABLE 8

| Cell strains | Accumulated product (g/L) | Optical purity (%) |
| --- | --- | --- |
| *Enterococcus faecalis* IFO 12966 | 6.90 | 99.0 |
| *Enterococcus casseliflavus* NRIC 0106 | 5.44 | 98.8 |
| *Lactobacillus collinoides* NRIC 1049 | 0.323 | 98.5 |
| *Lactobacillus viridescens* NRIC 1073 | 3.00 | 99.1 |
| *Leuconostoc mesenteroides* subsp. *dextranicum* NRIC 1085 | 3.11 | 99.0 |
| *Lactobacillus hilgardii* DSM 20051 | 0.706 | 99.1 |
| *Lactobacillus fructivorans* NRIC 0224 | 0.156 | 98.9 |

What is claimed is:

1. A method for producing an optically active mandelic acid derivative, which comprises the steps of:

(a) reacting a culture or cell bodies of a microorganism, or processed products thereof that can steroselectively reduce a phenylglyoxylic acid derivative of the formula (I) with said phenylglyoxylic acid derivative of the formula (I):

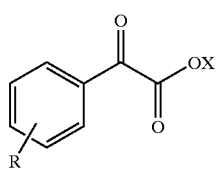

Formula I wherein: X is hydrogen, alkali metal, or alkaline earth metal; R indicates one or more substituents at ortho, meta, or para position, wherein the substituent is halogen, hydroxyl group, alkyl group having 1 to 3 carbon atoms, alkoxy group, thioalkyl group, amino group, nitro group, mercapto group, phenyl group, or phenoxy group;

(b) stereo-specifically reducing said phenylglyoxylic acid derivative with said microorganism culture, cell bodies or processed products to yield an optically active mandelic acid derivative of the formula (II):

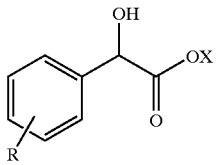

Formula II wherein: X and R is defined for formula (I); and (c) recovering said optically active mandelic acid derivative.

2. The method for producing an optically active mandelic acid derivative according to claim 1, wherein the resulting optically active mandelic acid is in the (R)-form, and the microorganism belongs to any of the genus selected from the group consisting of:

Candida;
Cryptococcus;
Hansenula;
Ogataea;
Pichia;
Rhodosporidium;
Rhodotorula;
Saccharomyces;
Trichosporon;
Yamadazyma;
Rhodococcus;
Amycolatopsis;
Alcaligenes;
Arthrobacter;
Brevibacterium;
Comamonas;
Corynebacterium;
Enterobacter;
Enterococcus;
Lactobacillus;
Leuconostoc;
Microbacterium;
Micrococcus;
Proteus; and
Pseudomonas.

3. The method for producing an optically active mandelic acid derivative according to claim 2, wherein the microorganism is selected from the group consisting of:

*Candida ernobii;*
*Candida gropengiesseri;*
*Candida magnoliae;*
*Candida sake;*
*Candida shehatae;*
*Candida silvatica;*
*Cryptococcus flavus;*
*Cryptococcus humicolus;*
*Cryptococcus marcerans;*

*Hansenula beckii;*
*Hansenula canadensis;*
*Hansenula glucozyma;*
*Ogataea pini;*
*Pichia carsonii;*
*Pichia fabianii;*
*Pichia haplophila;*
*Pichia subpelliculosa;*
*Rhodosporidium dacryodium;*
*Rhodosporidium diobovatum;*
*Rhodosporidium toruloides;*
*Rhodotorula glutinis;*
*Rhodotorula minuta;*
*Rhodotorula rubra;*
*Saccharomyces cerevisiae;*
*Trichosporon brassicae;*
*Trichosporon pullulans;*
*Yamadazyma castillae;*
*Yamadazyma nakazawae* var. *akitaensis;*
*Yamadazyma scolyti;*
*Rhodococcus erythropolis;*
*Rhodococcus fascians;*
*Rhodococcus obuensis;*
*Rhodococcus rhodochrous;*
*Amycolatopsis orientalis* subsp. *orientalis;*
*Alcaligenes* sp.;
*Arthrobacter protophormiae;*
*Brevibacterium iodinum;*
*Comamonas testosteroni;*
*Corynebacterium ammoniagenes;*
*Enterobacter cloacae;*
*Enterococcus casseliflavus;*
*Enterococcus faecalis;*
*Enterococcus hirae;*
*Lactobacillus viridescens;*
*Lactobacillus mali;*
*Lactobacillus collinoides;*
*Lactobacillus fructivorans;*
*Lactobacillus hilgardii;*
*Leuconostoc mesenteroides* subsp. *dextranicum;*
*Micrococcus luteus;*
*Proteus vulgaris;* and
*Pseudomonas diminuta.*

4. The method for producing an optically active mandelic acid derivative according to claim 1, wherein the resulting optically active mandelic acid is in the (S)-form, and the microorganism belongs to any of the genus selected from the group consisting of:

Rhodosporidium;

Lactobacillus;

Leuconostoc;

Microbacterium; and

Pseudomonas.

5. The method for producing an optically active mandelic acid derivative according to claim 4, wherein the microorganism is selected from the group consisting of:

*Rhodosporidium daryoidum;*

*Lactobacillus halotolerans;*

*Leuconostoc mesenteroides* subsp. *cremoris;*

*Microbacterium lacticum;* and

*Pseudomonas* sp.

6. The method for producing an optically active mandelic acid derivative according to claim 1, wherein the phenylglyoxylic acid derivative of Formula I has at least one R substituent at the ortho position.

7. The method for producing an optically active mandelic acid derivative according to claim 6, wherein the R substituent comprises a halogen at the ortho position.

8. The method for producing an optically active mandelic acid derivative according to claim 1, wherein the phenylglyoxylic acid derivative of Formula I has at least one R substituent at the meta position.

9. The method for producing an optically active mandelic acid derivative according to claim 8, wherein the R substituent comprises a halogen at the meta position.

* * * * *

UNITED STATES PATENT AND TRADEMARK OFFICE
CERTIFICATE OF CORRECTION

PATENT NO.    : 6,777,224 B2
DATED         : August 17, 2004
INVENTOR(S)   : Kazuya Mitsuhashi et al.

It is certified that error appears in the above-identified patent and that said Letters Patent is hereby corrected as shown below:

<u>Title page,</u>
Insert Item -- [30]    Foreign Application Priority Data,
        Oct. 24, 2001   [JP]   Japan...................2001-326060
        Feb. 07, 2002   [JP]   Japan...................2002-31544 --

Signed and Sealed this

Fourth Day of January, 2005

JON W. DUDAS
*Director of the United States Patent and Trademark Office*